United States Patent [19]
Yanni et al.

[11] Patent Number: 5,668,133
[45] Date of Patent: *Sep. 16, 1997

[54] OPHTHALMIC COMPOSITIONS COMPRISING EMEDASTINE AND METHODS FOR THEIR USE

[75] Inventors: John M. Yanni, Burleson; Stella M. Robertson, Arlington, both of Tex.; Shigetoshi Okumura, Nara, Japan; Hitoshi Tanaka, Nara-ken, Japan; Tadayuki Saito, Osaka, Japan

[73] Assignee: Alcon Laboratories, Inc., Fort Worth, Tex.

[*] Notice: The term of this patent shall not extend beyond the expiration date of Pat. No. 5,441,958.

[21] Appl. No.: 445,850

[22] Filed: May 22, 1995

Related U.S. Application Data

[63] Continuation-in-part of Ser. No. 163,973, Dec. 8, 1993, Pat. No. 5,441,958.
[51] Int. Cl.$^6$ .................................................. A61K 31/50
[52] U.S. Cl. ............................................. 514/253; 514/912
[58] Field of Search ............................... 514/253, 912

[56] References Cited

U.S. PATENT DOCUMENTS 4,430,343  2/1984  Iemura et al. .
5,192,780  3/1993  York et al. .

OTHER PUBLICATIONS

Miller, J. et al., "Antazoline phosphate and naphazoline hydrochloride, singly and in combination for the treatment of allergic conjunctivitis–a controlled, double-blind clinical trial," *Ann. Allergy.*, 35:81–86 (1975).

Vandewalker, M.L., et al., "Efficacy of Vasocon–A and its components with conjunctival provaction testing (CPT)," *J. Allergy Clin. Immunol.*, 83:302 (1989).

Abelson, M.B. et al., "Effects of topically applied ocular decongestant and antihistamine," *Am. J. Ophthalmol.*, 90:254–257 (1980).

DeChant, K.L. and K. L. Goa, "Levocabastine. A review of its pharmacological properties and therapeutic potential as a topical antihistamine in allergic rhinitis and conjunctivitis, "*Drugs*, 41:202–224 (1991).

Berdy et al., "Allergic conjunctivitis: A survey of new antihistamines," *J. Ocular Pharmacol.*, 7:313–324 (1991).

Yanni et al., "Effect of Lodoxamide on in vitro and in vivo conjunctival immediate hypersensitivity responses in rats," *Int. Arch. Allergy Immunol.*, 101:102–106 (1993).

Dunnett, C.W., "A multiple comparison procedure for comparing treatments with a control," *J. Am. Stat. Assoc.*, 50:1096–1121 (1955).

Bliss, C. and E. Gjorgy, *Vitamin Methods*, vol. 2, pp. 445–610, Academic Press, Inc. New York (1951).

*Primary Examiner*—Zohreh Fay
*Attorney, Agent, or Firm*—Sally Yeager

[57] ABSTRACT

Topical ophthalmic compositions comprising 1-(2-ethoxyethyl)-2-(4-methyl-1-homopiperazinyl)-benzimidazole and its ophthalmically acceptable acid addition salts have been found to be useful in treating ocular allergies, especially allergic conjunctivitis, giant papillary conjunctivitis, and vernal conjunctivitis.

5 Claims, No Drawings

OPHTHALMIC COMPOSITIONS COMPRISING EMEDASTINE AND METHODS FOR THEIR USE

This is a continuation-in-part of U.S. patent application Ser. No. 08/163,973, filed Dec. 8, 1993 now U.S. Pat. No. 5,441,958.

BACKGROUND OF THE INVENTION

The present invention relates to the field of ophthalmology, particularly the topical treatment of ocular allergies. Most particularly, the present invention relates to ophthalmic compositions comprising 1-(2-ethoxyethyl)-2-(4-methyl-1-homopiperazinyl)-benzimidazole, otherwise known as emedastine, and its ophthalmically acceptable acid addition salts and methods for their use.

Allergic conjunctivitis is frequently characterized by ocular pruritus (itching), erythema (inflammatory redness), edema and tearing. This condition is one of the most frequently treated by ophthalmologists, optometrists and allergists. To date, treatment has been primarily through the use of topically applied histamine $H_1$ antagonists in combination with α-agonists. See, for example, the following articles:

1. Miller, J. and E. H. Wolf, "Antazoline phosphate and naphazoline hydrochloride, singly and in combination for the treatment of allergic conjunctivitis—a controlled, double-blind clinical trial." Ann. Allergy, 35:81–86 (1975).
2. Vandewalker, M. L. et al., "Efficacy of Vasocon-A and its components with conjunctival provocation testing (CPT)" J. Allergy Clin. Immunol., 83:302 (1989).
3. Abelson, M. B. et al., "Effects of topically applied ocular decongestant and antihistamine." Am. J. Ophthalmol 90:254–257 (1980).

Recent studies indicate that the antihistamine levocabastine exhibits clinical activity in patients with allergic conjunctivitis without the addition of a vasoconstrictor. See, Dechant, K. L. and K. L. Goa, "Levocabastine. A review of its pharmacological properties and therapeutic potential as a topical antihistamine in allergic rhinitis and conjunctivitis." Drugs 41:202–224 (1991). In addition, it has recently been demonstrated that $H_1$ antagonists are effective in relieving conjunctival injection (hyperemia) and erythema, as well as pruritus. See, Berdy, G. J. et al., "Allergic conjunctivitis: A survey of new antihistamines." J. Ocular Pharmacol. 7:313–324 (1991).

Although there are many different antihistamines available for systemic treatment of allergies and related ailments, many such antihistamines are not suitable for topical ophthalmic use because of limited ocular bioavailability. For example, terfenadine (Seldane®, made by Marion Merrell Dow), astemizole (Hismanal®, made by Janssen Pharmaceutica) and loratadine (Claritin®, made by Schering) all have good systemic activity; however, terfenadine has little or no local ocular activity, and astemizole and loratadine each have greatly reduced local ocular activity (as compared to their systemic activity). A need therefore exists for an antihistamine having good local ocular activity and having minimal side effects.

SUMMARY OF THE INVENTION

It has now been unexpectedly discovered that topical ophthalmic compositions comprising 1-(2-ethoxyethyl)-2-(4-methyl-1-homopiperazinyl)-benzimidazole and its ophthalmically acceptable acid addition salts are useful in treating ocular allergies, especially allergic conjunctivitis (acute and chronic atopic conjunctivitis) and the pruritus and/or edema associated with giant papillary conjunctivitis and vernal conjunctivitis. In particular, the components of the present invention have good local activity, with quick onset of action and fairly long duration of action.

DETAILED DESCRIPTION OF THE INVENTION

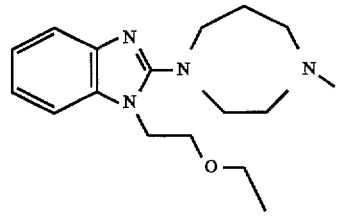

1-(2-Ethoxyethyl)-2-(4-methyl-1-homopiperazinyl)-benzimidazole, otherwise known as emedastine, is pictured above and is disclosed and claimed in U.S. Pat. No. 4,430,343 (Iemura et al.), along with numerous other benzimidazole derivatives. Iemura et al. disclose the use of this class of compounds as anti-allergics and antihistamines, but do not disclose the ophthalmic use of these types of compounds. U.S. Pat. No. 5,192,780 (York et al.) discloses the use of combinations of antiallergics and antihistamines to prevent and treat ophthalmic allergic responses. To the extent that Iemura et al. disclose methods for preparation of the compounds of the present invention, that patent is hereby incorporated by reference herein.

The compounds useful in the present invention include emedastine and its ophthalmically acceptable acid addition salts. Ophthalmically acceptable acid addition salts include salts of organic or inorganic acids, such as maleic acid, fumaric acid, hydrochloric acid or sulfuric acid. These salts may be formed conventionally. It is preferred to use the difumarate salt of emedastine.

In forming compositions for topical administration, the compounds of the present invention are generally formulated at between about 0.0001 and about 1.0 percent by weight (wt %) solutions in water at a pH between about 6 and about 8. The compounds are preferably formulated at between about 0.005 and about 0.2 wt % and, most preferably, between about 0.05 and about 0.2 wt %. While the precise regimen is left to the discretion of the clinician, it is recommended that the resulting compositions be topically applied by placing one or more drops in each eye one or more times a day.

The compositions of the present invention may be prepared by combining one or more of the compounds of the present invention with a suitable vehicle to form a solution, dispersion or gel. The compositions of the present invention may also include one or more ingredients conventionally found in ophthalmic formulations, such as preservatives (e.g., benzalkonium chloride or thimerosal), viscosity-imparting agents (e.g., polyvinyl alcohol or hydroxypropyl methylcellulose) and tonicity agents (e.g., sodium chloride or mannitol). The compositions will typically also include buffering agents to maintain the pH within physiological pH (between 6 and 8); however, it has been found that citrate, acetate and phosphate buffers are not compatible with the compounds of the present invention, as these buffering agents, particularly phosphate buffers, compromise the stability and solubility of the compounds. It is therefore preferred to use Tris (tri(hydroxymethyl)aminomethane) as a buffering agent in the compositions of the present invention. Hydrochloric acid or sodium hydroxide will normally be used to adjust the pH of the resultant compositions.

EXAMPLE 1

The following examples are typical compositions of the present invention. These formulations may be prepared in accordance with procedures known to those skilled in the art.

| INGREDIENT | FORMULA-TION A (wt %) | FORMULA-TION B (wt %) | FORMULAT-ION C (wt %) |
|---|---|---|---|
| Emedastine Difumarate | 0.177 | 0.0884 | 0.884 |
| Benzalkonium Chloride | 0.01 | 0.01 | 0.01 |
| Disodium EDTA | 0.01 | 0.01 | 0.01 |
| Tris(hydroxymethyl)-aminomethane | 0.5 | 0.5 | 0.5 |
| Sodium Chloride | 0.64 | 0.66 | 0.46 |
| Hydroxypropyl Methylcellulose (2910) (E4M) | 0.25 | 0.25 | 0.25 |
| NaOH and/or HCl | q.s. to pH 7.4 | q.s. to pH 7.4 | q.s. to pH 7.4 |
| Purified Water | q.s. to 100% | q.s. to 100% | q.s. to 100% |

EXAMPLE 2

The topical ocular antihistaminic effect of emedastine difumarate was assessed in a model of histamine induced vascular permeability in guinea pig conjunctiva. The potency of emedastine difumarate in this model was then compared with those of reference antihistamines.

Male Dunkin Hartley Viral Antibody Free outbred guinea pigs (Charles River Labs, Portage, Mich.), weighing approximately 250–350 grams (6/group) were injected intravenously (i.v.) via the marginal ear vein with 1.0 mL of Evans Blue dye (1.0 mg/mL). Forty-five (45) minutes post dye injection, 20 μL of test compound or saline vehicle was applied topically to one eye of each experimental animal. Thirty minutes following topical drug application, the guinea pigs were anesthetized and challenged subconjunctivally with histamine (300 ng/10 μL). Responses were quantitated as described by Yanni et al. in *Int. Arch. Allergy Immunol.*, 101:102–106 (1993). Response scores from the treated groups were then compared with scores obtained in the saline-treated group using Dunnett's t test (Dunnett C. W., "A multiple comparison procedure for comparing treatments with a control." *J. Am. Stat. Assoc.* 50:1096–1121 (1955)). Regression analysis was used to determine relative potency (Bliss, C. and E. Gjorgy. In *Vitamin Methods*, Vol. 2, pp. 445–610, Academic Press, Inc., New York, 1951.).

TABLE 1

Effects of Emedastine Difumarate On Histamine-Induced Vascular Permeability In Guinea Pigs

| Compound | Pretreatment Interval | Concentration (wt %) | Percent Change | $ED_{50}$ (wt %) |
|---|---|---|---|---|
| NaCl | 1 min | 0.9 | — | — |
| Emedastine Difumarate | 1 min | 0.0001 | −44* | 0.0002 |
|  |  | 0.001 | −62* |  |
|  |  | 0.01 | −81* |  |
| NaCl | 30 min | 0.9 | — | — |
| Emedastine Difumarate | 30 min | 0.000006 | −28 | 0.000035 |
|  |  | 0.00006 | −58* |  |
|  |  | 0.0006 | −93* |  |
| NaCl | 2 hr | 0.9 | — | — |
| Emedastine Difumarate | 2 hr | 0.001 | −35* | 0.0029 |
|  |  | 0.005 | −53* |  |
|  |  | 0.01 | −72* |  |
| NaCl | 4 hr | 0.9 | — | — |
| Emedastine Difumarate | 4 hr | 0.001 | −9 | 0.019 |
|  |  | 0.001 | −39* |  |
|  |  | 0.1 | −84* |  |
|  |  | 1.0 | −95* |  |
| NaCl | 8 hr | 0.9 | — | — |
| Emedastine Difumarate | 8 hr | 0.01 | −5 | 0.19 |
|  |  | 0.05 | −33* |  |
|  |  | 0.1 | −43* |  |
|  |  | 0.5 | −66* |  |
|  |  | 1.0 | −71* |  |

*$p < 0.01$, Dunnett's t test

As shown in Table 1, above, topical ocular administration of emedastine difumarate at 1 minute, 30 minutes, 2, 4 or 8 hours prior to subconjunctival histamine challenge inhibited in concentration-dependent fashion the vascular permeability response. Calculated $ED_{50}$ values obtained from these data were 0.0002%, 0.000035%, 0.0029%, 0.019% and 0.19% respectively. These results indicate that emedastine difumarate possesses a rapid onset and an acceptable duration of action following topical ocular administration.

EXAMPLE 3

Comparisons of emedastine difumarate's potency with those of reference antihistamines utilizing topical ocular administration and treatment intervals of 1 minute or 30 minutes in the in vivo testing paradigm described above were completed.

TABLE 2

Effects of $H_1$ Antagonists Applied Topically Immediately Prior to Histamine Challenge

| Compound | Concentration (wt %) | Wheal Area × Intensity | Potency | Compound | Concentration (wt %) | Wheal Area × Intensity | Potency** |
|---|---|---|---|---|---|---|---|
| NaCl | 0.9 | 308 ± 20 | — | — | — | — | — |
| Emedastine Difumarate | 0.0001 | 166 ± 14* | 1.0 | Pyrilamine | 0.0001 | 220 ± 17* | 0.737[a] |
|  | 0.001 | 104 ± 20* |  |  | 0.001 | 94 ± 23* |  |
|  | 0.01 | 57 ± 16* |  |  | 0.01 | 41 ± 20* |  |
| NaCl | 0.9 | 276 ± 10 | — | — | — | — | — |

TABLE 2-continued

Effects of H₁ Antagonists Applied Topically Immediately Prior to Histamine Challenge

| Compound | Concentration (wt %) | Wheal Area × Intensity | Potency | Compound | Concentration (wt %) | Wheal Area × Intensity | Potency** |
|---|---|---|---|---|---|---|---|
| Emedastine Difumarate | 0.0001 | 159 ± 26* | 1.0 | Ketotifen | 0.0001 | 210 ± 11* | 0.288 (0.147–0.565) |
| | 0.001 | 141 ± 38* | | | 0.001 | 138 ± 21* | |
| | 0.01 | 45 ± 18* | | | 0.01 | 89 ± 22* | |
| | | | | | 0.1 | 33 ± 22* | |
| | | | | Pheniramine | 0.001 | 181 ± 16* | 0.130 (0.054–0.326) |
| | | | | | 0.01 | 87 ± 40* | |
| | | | | | 0.1 | 59 ± 23* | |
| NaCl | 0.9 | 285 ± 19 | — | — | — | — | — |
| Emedastine Difumarate | 0.0001 | 159 ± 31* | 1.0 | Antazoline | 0.0001 | 244 ± 14* | 0.060 (0.023–0.132) |
| | 0.001 | 109 ± 14* | | | 0.001 | 178 ± 42* | |
| | 0.01 | 55 ± 12* | | | 0.01 | 115 ± 6* | |
| NaCl | 0.9 | 336 ± 78 | — | — | — | — | — |
| Emedastine Difumarate | 0.01 | 26 ± 27* | 1.0 | Levocabastine | 0.05 | 231 ± 58 | |

*$p < 0.05$, Dunnett's t test
**(95% Confidence Limits)
ªValue represents approximate potency; confidence limits were not calculated because of lack of parallelism between the regression lines.

The results shown in Table 2, above, demonstrate that emedastine difumarate is 3, 8, and 17 times more potent than ketotifen, pheniramine, and antazoline, respectively, and approximately equipotent to pyrilamine when compounds are administered topically 1 minute before histamine challenge. Levocabastine (0.05%) failed to attenuate significantly the histamine-induced vascular permeability response in the conjunctiva when administered topically 1 minute before histamine injection.

TABLE 3

Relative Potencies of Topically Applied H₁ Antagonists in Histamine-Induced Vascular Permeability in Guinea Pigs

| Compound | Concentration (wt %) | Wheal Area × Intensity (X ± S.D.) | Potency | Compound | Concentration (wt %) | Wheal Area × Intensity (x ± S.D.) | Potency** |
|---|---|---|---|---|---|---|---|
| NaCl | 0.9 | 214 ± 41 | — | — | — | — | — |
| Emedastine Difumarate | 0.000006 | 154 ± 62 | 1.0 | Ketotifen | 0.0000007 | 157 ± 66 | 3.72 (0.973–11.892) |
| | 0.00006 | 91 ± 26* | | | 0.000007 | 108 ± 52* | |
| | 0.0006 | 16 ± 14* | | | 0.00007 | 61 ± 26* | |
| NaCl | 0.9 | 219 ± 20 | — | — | — | — | — |
| Emedastine Difumarate | 0.00001 | 191 ± 48 | 1.0 | Brompheniramine | 0.0001 | 167 ± 26* | 0.14 (0.078–0.263) |
| | 0.0001 | 104 ± 47* | | | 0.001 | 92 ± 44* | |
| | 0.001 | 8 ± 9* | | | 0.01 | 5 ± 8* | |
| NaCl | 0.9 | 217 ± 35 | — | — | — | — | — |
| Emecastine Difumarate | 0.00001 | 161 ± 68 | 1.0 | Chlorpheniramine | 0.0001 | 161 ± 57 | 0.13 (0.056–0.295) |
| | 0.0001 | 112 ± 58* | | | 0.001 | 76 ± 22* | |
| | 0.001 | 18 ± 23* | | | 0.01 | 9 ± 12* | |
| NaCl | 0.9 | 350 ± 31 | — | — | — | — | — |
| Emedastine Difumarate | 0.000001 | 265 ± 35* | 1.0 | Clemastine | 0.00001 | 283 ± 37* | 0.105 (0.063–0.176) |
| | 0.00001 | 165 ± 30* | | | 0.0001 | 131 ± 36* | |
| | 0.0001 | 70 ± 27* | | | 0.001 | 65 ± 28* | |
| | 0.001 | 6 ± 7* | | | 0.01 | 18 ± 8* | |
| NaCl | 0.9 | 194 ± 41 | — | — | — | — | — |
| Emedastine Difumarate | 0.000006 | 136 ± 42 | 1.0 | Pyrilamine | 0.00001 | 202 ± 46 | 0.099 (0.028–0.261) |
| | 0.00006 | 75 ± 22* | | | 0.0001 | 124 ± 49* | |
| | 0.0006 | 6 ± 7* | | | 0.001 | 75 ± 42* | |
| NaCl | 0.9 | 252 ± 30 | — | — | — | — | — |
| Emedastine Difumarate | 0.00001 | 191 ± 27* | 1.0 | Levocabastine | 0.0005 | 189 ± 66 | 0.01 (0.006–0.038) |
| | 0.0001 | 137 ± 24* | | | 0.005 | 116 ± 67* | |
| | 0.001 | 7 ± 9* | | | 0.05 | 56 ± 41* | |
| | | | | Pheniramine | 0.003 | 175 ± 53* | 0.0028ª |
| | | | | | 0.03 | 122 ± 33* | |
| | | | | | 0.3 | 56 ± 41* | |
| NaCl | 0.9 | 214 ± 34 | — | — | — | — | — |
| Emedastine | 0.00001 | 163 ± 32* | 1.0 | Diphenhydramine | 0.01 | 210 ± 23 | 0.0003 |

TABLE 3-continued

Relative Potencies of Topically Applied $H_1$ Antagonists in Histamine-Induced Vascular Permeability in Guinea Pigs

| Compound | Concentration (wt %) | Wheal Area × Intensity (X ± S.D.) | Potency | Compound | Concentration (wt %) | Wheal Area × Intensity (x ± S.D.) | Potency** |
|---|---|---|---|---|---|---|---|
| Difumarate | | | | | | | (0.00018–0.00051) |
| | 0.0001 | 98 ± 22* | | | 0.1 | 127 ± 25* | |
| | 0.001 | 12 ± 19* | | | 1.0 | 53 ± 31* | |
| NaCl | 0.9 | 287 ± 20 | — | — | | — | — |
| Emedastine | 0.00001 | 197 ± 57* | 1.0 | Antazoline | 0.01 | 205 ± 61* | 0.00017ª |
| Difumarate | 0.0001 | 65 ± 32* | | | 0.1 | 145 ± 26* | |
| | 0.001 | 4 ± 4* | | | 1.0 | 91 ± 27* | |

*p < 0.05, Dunnett's t test
ªValues are approximate potencies; confidence limits were not calculated because of lack of parellelism between the regression lines
**(95% Confidence limits)

Results obtained using a 30 minute treatment interval are presented in Table 3. Emedastine difumarate is equipotent to ketotifen, and 7, 7, 10, 10, 100, and 3333 times more potent than brompheniramine, chlorpheniramine, clemastine, pyrilamine, levocabastine and diphenhydramine, respectively. In addition, these studies demonstrate that emedastine difumarate is approximately 357 and 5813 times more potent than pheniramine and antazoline, respectively. (Approximate potency has been calculated due to lack of parallelism.)

EXAMPLE 4

Emedastine difumarate was evaluated for its ability to inhibit a passive conjunctival immediate hypersensitivity response following topical ocular administration.

Guinea pigs (5–8/group) were passively sensitized with anti-ovalbumin serum injected subconjunctivally in one eye. Twenty-four hours after passive sensitization, ovalbumin (OA) was administered either i.v. or topically to the eye.

The allergic response following i.v. antigen challenge was assessed as follows: thirty minutes prior to challenge, animals received 20 μL of emedastine difumarate or saline applied topically to the eye. Guinea pigs were then challenged i.v. via the marginal ear vein with 1.0 mL of a solution containing 100 μg of OA and 1 mg of Evans Blue dye. Responses were quantitated as previously described in Example 2.

For assessment of the allergic response following topical ocular antigen challenge, 20 μL of ovalbumin (1.0 wt %) was administered to the sensitized eye 5 minutes after topical ocular application of emedastine difumarate or saline (20 μL). Thirty minutes later, the reaction was quantitated, using the following scoring scheme (maximum score per animal=10):

Congestion (refers to palpebral and bulbar conjunctiva):
 0—Normal
 1—Pink conjunctiva
 2—Red conjunctiva
 3—Dark red conjunctiva; petechiae present
Swelling:
 0—None
 1—Any swelling on lower lid only
 2—Swelling upper and lower lid, lids partially closed
 3—Lids everted, very swollen, lids at least half closed
 4—Swelling of both lids and side of face
Discharge:
 0—None
 1—Glazed, glassy appearance
 2—Moist lids and surrounding hair
 3—Moist lids and surrounding hair, thicker mucous-like

TABLE 4

Effect of Emedastine Difumarate on Passive Anaphylaxis in Guinea Pig Conjunctiva

| Antigen Challenge | Compound | Conc. (wt %) | % Change | $ED_{50}$ (wt %) |
|---|---|---|---|---|
| i.v. | NaCl | 0.9 | — | — |
| | Emedastine | 0.0001 | −41 | 0.00022 |
| | | 0.001 | −66* | |
| | | 0.01 | −96* | |
| topical ocular | NaCl | 0.9 | — | — |
| | Emedastine | 0.0001 | −29* | 0.0046 |
| | | 0.001 | −45* | |
| | | 0.01 | −51* | |
| | | 0.1 | −67* | |

*p < 0.05, Dunnett's t test

As shown in Table 4, above, significant reductions of the allergic response were observed in animals treated with 0.001% and 0.01% solutions of emedastine difumarate 30 minutes before i.v. antigen challenge. The $ED_{50}$ value for emedastine difumarate obtained from this experiment was 0.00022%. In an experiment in which the allergic response was initiated by topical ocular antigen challenge and quantified by clinical scoring, emedastine difumarate administration 5 minutes before antigen challenge produced concentration-dependent reductions in the severity of the hypersensitivity response (See Table 4, above). Significant attenuation was observed with concentrations ranging from 0.0001% to 0.1% ($ED_{50}$=0.0046%).

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed:

1. A method for treating the pruritus and/or edema associated with giant papillary conjunctivitis and vernal conjunctivitis, comprising topically administering to an affected eye an antihistaminic effective amount of a compound selected from the group consisting of 1-(2-ethoxyethyl)-2-(4-methyl-1-homopiperazinyl)-benzimidazole and its ophthalmically acceptable acid addition salts.

2. The method of claim 1, wherein said compound is present at a concentration between about 0.0001 and about 1.0 wt %.

3. The method of claim 2, wherein said compound is present at a concentration between about 0.005 and about 0.2 wt %.

4. The method of claim 3, wherein said compound is present at a concentration between about 0.05 and about 0.2 wt %.

5. The method of claim 1, wherein the compound comprises the difumarate salt of 1-(2-ethoxyethyl)-2-(4-methyl-1-homopiperazinyl)-benzimidazole.

* * * * *